(12) United States Patent
Ivey et al.

(10) Patent No.: US 7,776,522 B2
(45) Date of Patent: Aug. 17, 2010

(54) METHODS FOR DIAGNOSING ONCOGENIC HUMAN PAPILLOMAVIRUS (HPV)

(75) Inventors: Richard Ivey, Parkton, MD (US); Stephen J. Lovell, Lutherville, MD (US); Robert Rosenstein, Elicott City, MD (US); Thomas Gentle, St. Michael, MN (US); Song Shi, Reisterstown, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 12/108,550

(22) Filed: Apr. 24, 2008

(65) Prior Publication Data

US 2009/0269732 A1     Oct. 29, 2009

(51) Int. Cl.
    *C12Q 1/68* (2006.01)
(52) U.S. Cl. ......................................... 435/5
(58) Field of Classification Search ................. None
    See application file for complete search history.

(56) References Cited

U.S. PATENT DOCUMENTS

| | | |
|---|---|---|
| 6,675,104 B2 | 1/2004 | Paulse et al. |
| 6,692,916 B2 | 2/2004 | Bevilacqua et al. |
| 6,756,483 B1 | 6/2004 | Bergmann et al. |
| 6,861,234 B1 * | 3/2005 | Simard et al. ........... 435/29 |
| 2003/0004402 A1 | 1/2003 | Hitt et al. |
| 2003/0027176 A1 | 2/2003 | Dailey |
| 2003/0057106 A1 | 3/2003 | Shen et al. |
| 2003/0219771 A1 | 11/2003 | Bevilacqua et al. |
| 2004/0096917 A1 * | 5/2004 | Ivey et al. ........... 435/7.32 |
| 2004/0097460 A1 | 5/2004 | Ivey et al. |
| 2004/0106142 A1 | 6/2004 | Ivey et al. |
| 2004/0121343 A1 | 6/2004 | Buechler et al. |
| 2004/0121350 A1 | 6/2004 | Anderberg et al. |
| 2004/0126767 A1 | 7/2004 | Anderberg et al. |
| 2004/0133352 A1 | 7/2004 | Bevilacqua et al. |
| 2004/0157242 A1 | 8/2004 | Ivey et al. |
| 2004/0175754 A1 | 9/2004 | Bar-Or et al. |
| 2004/0219568 A1 | 11/2004 | Bevilacqua et al. |
| 2004/0225447 A1 | 11/2004 | Bevilacqua et al. |
| 2004/0225449 A1 | 11/2004 | Bevilacqua et al. |
| 2004/0253637 A1 | 12/2004 | Buechler et al. |
| 2005/0130242 A1 | 6/2005 | Bergmann et al. |
| 2005/0164238 A1 | 7/2005 | Valkirs et al. |

FOREIGN PATENT DOCUMENTS

| | | |
|---|---|---|
| WO | 9428418 A1 | 12/1994 |
| WO | 0242733 A2 | 5/2002 |
| WO | 02088744 A2 | 11/2002 |
| WO | 2004044554 A2 | 5/2004 |
| WO | 2004044555 A2 | 5/2004 |
| WO | 2004044556 A2 | 5/2004 |
| WO | 2004059293 A2 | 7/2004 |

OTHER PUBLICATIONS

Adam et al. "Serum Protein Fingerprinting Coupled with a Pattern-matching Algorithm Distinguishes Prostate Cancer from Benign Prostate Hyperplasia and Healthy Men", Cancer Research, Jul. 1, 2002, vol. 62, pp. 3609-3614.
Bright et al., "Rapid typing of bacteria using matrix-assisted laser desorption ionisation time-of-flight mass spectrometry and pattern recognition software," J. Microbiol. Methods, 2002, vol. 48, pp. 127-138.
Dalluge, "Mass spectrometry for direct determination of proteins in cells: applications in biotechnology and microbiology," Fresenius J. Anal. Chem., 2000, vol. 366, pp. 701-711.
Hagberg, "From magnetic resonance spectroscopy to classification of tumors. A review of pattern recognition methods," NMR Biomed., 1998, vol. 11, pp. 148-156.
Petricoin et al., "Use of proteomic patterns in serum to identify ovarian cancer," Lancet, 2002, vol. 359, pp. 572-577.
Presto Elgstoen et al., "Potential of capillary electrophoresis, tandem mass spectrometry and coupled capillary electrophoresis-tandem mass spectrometry as diagnostic tools," J. Chromatogr. A, 2001, vol. 914, pp. 265-275.
Takala et al., "Markers of inflammation in sepsis," Annuls Med., 2002, vol. 34, pp. 614-623.
Tan et al., "The gene expression fingerprint of human heart failure," Proc. Nat'l Acad. Sci. USA, 2000, vol. 99, pp. 11387-11392.
Wagner et al., "Daily prognostic estimates for critically ill adults in intensive care units: Results from a prospective, multicenter, inception cohort analysis," Critical Care Medicine, 1994, vol. 22 (9), pp. 1359-1372.
Wei et al., "Desorption-ionization mass spectrometry on porous silicon," Nature, 1999, vol. 399, pp. 243-246.

* cited by examiner

*Primary Examiner*—Ali R. Salimi
(74) *Attorney, Agent, or Firm*—Scott J. Rittman

(57) ABSTRACT

Methods for diagnosis of HPV infection in a subject are provided. HPV infection in a subject can be determined by generating mass profile data for a biological sample from the subject and correlating the mass profile data with reference mass profiles to detect the presence or absence, and/or quantity of at least one biomarker associated with HPV infection. Methods for detecting at least one biomarker associated with HPV infection in a biological sample are also provided.

10 Claims, 2 Drawing Sheets

METHODS FOR DIAGNOSING ONCOGENIC HUMAN PAPILLOMAVIRUS (HPV)

FIELD

The present invention relates to the diagnosis of human papillomavirus (HPV). More particularly, the present invention provides a method for diagnosis of HPV by detecting the presence or absence of at least one biomarker associated with HPV and/or the quantity thereof.

BACKGROUND

Cervical cancer is the second most common cancer diagnosis in women and is linked to high-risk human papillomavirus infection 99.7% of the time. Currently, 12,000 new cases of invasive cervical cancer are diagnosed in US women annually, resulting in 5,000 deaths each year. Furthermore, there are approximately 400,000 cases of cervical cancer and close to 200,000 deaths annually worldwide. Human papillomaviruses (HPVs) are one of the most common causes of sexually transmitted disease in the world. Overall, 50-75% of sexually active men and women acquire genital HPV infections at some point in their lives. An estimated 5.5 million people become infected with HPV each year in the US alone, and at least 20 million are currently infected. The more than 100 different isolates of HPV have been broadly subdivided into high-risk and low-risk subtypes based on their association with cervical carcinomas or with benign cervical lesions or dysplasias.

HPVs are a diverse group of relative small DNA viruses and are the etiologic agents of epithelial outgrowths, or papillomas. The DNAs of papilloma virus can be divided into the Early Region Genes (E5, E6, E7) and Late Region Gene (L1, L2) where E regions are postulated to encode proteins needed for replication and transformation while the L regions to encode the viral capsid proteins. These proteins related to HPV are biomarkers used to detect HPV in samples. In humans, specific papillomavirus types have been detected in, and associated with over 99% of cervical cancer biopsies. These are considered the high-risk types and include, in orders of prevalence, HPV types-16, 18, 31, 33, 35, 45, 51, 52, and 56.

A number of lines of evidence point to HPV infections as the etiological agents of cervical cancers. Multiple studies in the 1980's reported the presence of HPV variants in cervical dysplasias, cancer, and in cell lines derived from cervical cancer. Further research demonstrated that the E6-E7 region of the genome from oncogenic HPV 18 is selectively retained in cervical cancer cells, suggesting that HPV infection could be causative and that continued expression of the E6-E7 region is required for maintenance of the immortalized or cancerous state. The following year, Sedman et al. demonstrated that the E6-E7 genes from HPV 16 were sufficient to immortalize human keratinocytes in culture. Barbosa et al. demonstrated that although E6-E7 genes from high risk HPVs could transform cell lines, the E6-E7 regions from low risk, or non-oncogenic variants such as HPV 6 and HPV 11 were unable to transform human keratinocytes. More recently, Pillai et al. examined HPV 16 and 18 infection by in situ hybridization and E6 protein expression by immunocytochemistry in 623 cervical tissue samples at various stages of tumor progression and found a significant correlation between histological abnormality and HPV infection.

Current treatment paradigms are focused on the actual cervical dysplasia rather than the underlying infection with HPV. Women are screened by physicians annually for cervical dysplasia and are treated with superficial ablative techniques, including cryosurgery, laser ablation and excision. As the disease progresses, treatment options become more aggressive, including partial or radical hysterectomy, radiation or chemotherapy. A significant unmet need exists for early and accurate diagnosis of oncogenic HPV infection as well as for treatments directed at the causative HPV infection, preventing the development of cervical cancer by intervening earlier in disease progression. Human papillomaviruses characterized to date are associated with lesions confined to the epithelial layers of skin, or oral, pharyngeal, respiratory, and, most importantly, anogenital mucosae. Specific human papillomavirus types, including HPV 6 and 11, frequently cause benign mucosal lesions, whereas other types such as HPV 16, 18, and a host of other strains, are predominantly found in high-grade lesions and cancer. Individual types of human papillomaviruses (HPV) which infect mucosal surfaces have been implicated as the causative agents for carcinomas of the cervix, anus, penis, larynx and the buccal cavity, occasional periungal carcinomas, as well as benign anogenital warts. The identification of particular HPV types is used for identifying patients with premalignant lesions who are at risk of progression to malignancy. Although visible anogenital lesions are present in some persons infected with human papillomavirus, the majority of individuals with HPV genital tract infection do not have clinically apparent disease, but analysis of cytomorphological traits present in cervical smears can be used to detect HPV infection.

At the present time, the primary methodology for public health screening for cervical cancer has been the annual Pap smear test. The main problems associated with the Pap smear test have been the high rate of false negatives. Nucleic acid assays developed for HPV screening offer much better sensitivity and specificity. They include Souther blotting, Dot blot, Filter in situ Hybridization (FISH), In situ hybridization, Hybrid capture and Polymerase chain reaction (PCR). Among the nucleic acid assays, Digene's Hybrid capture assay and Roche's PCR based assay hold most of the market. However, both assays tend to suffer from high cost, sampling difficulties and contamination issues. In addition, the oncogenicity of HPV has been shown to be protein based. As such, detection of HPV DNA or RNA may lead to unnecessary medical procedures that the body's immune system may solve naturally.

Recently, immunoassays have been developed for HPV diagnostic application. E6-Associated Protein (E6-AP), a polypeptide that stably associates with E6 in the presence or absence of p53 has been isolated and proposed to be used to detect the presence of "high risk" human papillomaviruses (U.S. Pat. No. 5,914,384). A broad antibody based sandwich assay for detection of HPV protein, particularly HPV-E6 or HPV-E7 was described in U.S. Pat. No. 6,214,541 B1. U.S. Pat. No. 4,777,239 describes a series of 17 synthetic peptides which are said to be capable of raising antibodies to HPV-16 and thus may be useful for diagnostic purpose. EU Patent 0 412 762 describes polypeptides which are antagonists of biochemical interaction of HPV E7 protein and the retinoblastoma gene protein, and which are said to be useful in the treatment of genital warts and cervical cancer. U.S. Patent Application Publication No. US 2003/0064477 A1 describes a putative tumor suppressor protein designated E6-TP1 (for E6-targeted protein) that can act as a therapeutic agent for treatment or prevention of HPV-associated carcinomas. U.S. Patent Application Publication No. US 2004/0110925 A1 describes an isolated protein sequence or peptide from HPV for detecting or diagnosing cancer or cellular abnormalities, said isolated proteins sequence or peptide selected from the group consisting of: E2, E6, E7, and E8 regions of HPV type 16, 18, 31, 33, 35, 45, 51, 52, 56, and 58. U.S. Patent Application Publication No. US 2004/0018487 A1 describes a method of detecting the presence of an oncogenic HPV E6 protein in a sample by capturing an oncogenic HPV E6 protein with a PDZ domain polypeptide. Each of these publications and all publications mentioned herein are incorporated in their entirety by reference herein.

Traditional assay methods also fail to provide a single test to detect all (or even more than one) of the different types of biomarkers which are associated with HPV. Most of the immunoassays presently used, for example, can only detect the native E6 or E7 proteins of human papillomavirus types 16, 18, 31, 33, 35, 45, 51, 52, or 56, which make the sampling procedure more difficult. Detection of E6 protein using antibodies is difficult because E6 that is made in a human cells contains a number of structural modifications, e.g., disulfide bonds and phosphate groups, that cause wild-type E6 protein made in bacterial systems, or chemically synthesized E6 peptides, to not recognize E6 protein in human cells. Thus, one would have to run many separate assays to have any chance of a thorough detection technique and yet still risk a detection error.

Traditional assay methods also fail to detect more than one type of protein in a single testing. Immunoassays, for example, require multiple runs of a protein array, without cross-reactions.

It would therefore be advantageous to have a new diagnostic tool for the detection of HPV in a patient that provides a single test to detect more than one or all of the different biomarkers which are associated with HPV, higher sensitivity and/or specificity for the detection of HPV than other methods, a lower false-positive rate of diagnosis, and/or a reduction in the number of patients requiring further screening. It would also be advantageous to use the capabilities of SELDI-MS to detect and identify biomarkers capable of correctly classifying samples as those originating from patients having HPV.

SUMMARY OF THE INVENTION

Accordingly, a feature of the present invention is to provide methods for diagnosing human pappillomavirus (HPV) infection in a subject by detecting biomarkers (preferably checking for two or more biomarkers in a single test) associated with HPV in a biological sample from a subject.

Another feature of the present invention is to provide methods for diagnosing human pappillomavirus (HPV) infection in a subject that distinguishes biomarkers associated with HPV by differences in molecular weight.

Another feature of the present invention is to provide methods for diagnosing oncogenic human pappillomavirus (HPV) infection in a biological sample from a subject.

Another feature of the present invention is to provide methods for diagnosing human pappillomavirus (HPV) infection in a biological sample from a subject that requires little or no sample preparation.

To achieve the features and in accordance with the purposes of the present invention, as embodied and broadly described herein, the present invention, in part, relates to methods for the diagnosis of papillomavirus infection in a subject by generating mass profile data (e.g., mass spectrum) for a biological sample of a given subject, and correlating the mass profile data with a reference mass profile to detect the presence or absence, and/or the quantity of at least one biomarker associated with HPV.

DETAILED DESCRIPTION OF THE INVENTION

Figure 1:
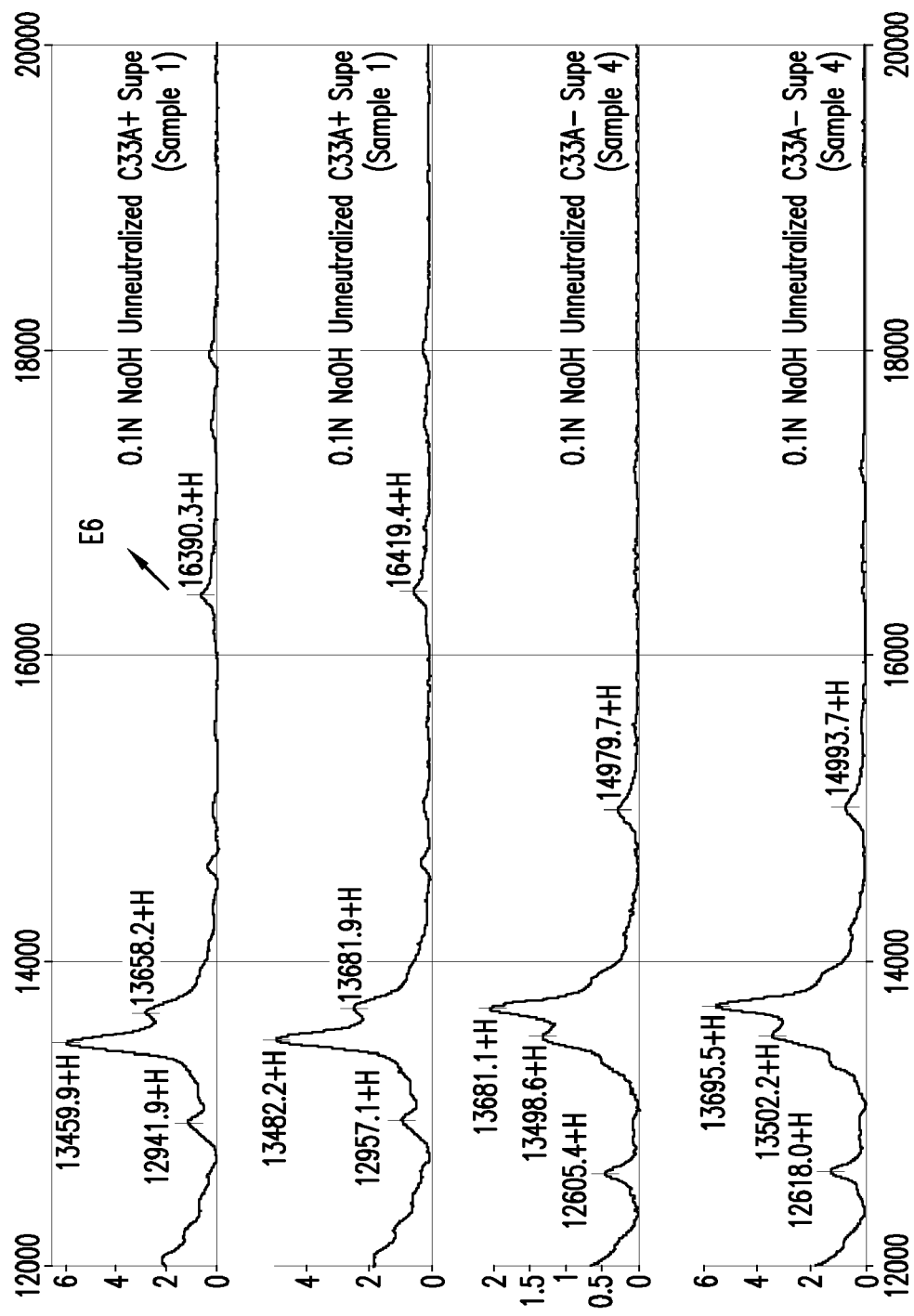
FIG. 1 shows mass spectral data for two different clinical samples containing cells from a cervical cancer cell line.

Methods of detecting/and or diagnosing human pappillomavirus (HPV) infection in a subject are disclosed. HPV infection in a subject can be diagnosed by detecting one or more biomarkers in a biological sample from the subject. Biomarkers associated with HPV infection can exist in a sample in a plurality of different forms, which traditional detection assays generally cannot distinguish between or cannot detect by way of a single assay. The method of the present invention permits separate identification and/or distinguishes between biomarkers and/or forms of a particular biomarker, and/or specifically detects and measures a desired form or forms of the biomarker.

According to one or more embodiments, methods for diagnosing human pappillomavirus (HPV) infection in a subject can comprise generating mass profile data (e.g., mass spectrum) for a biological sample from the subject. Once mass profile data for a biological sample is generated, the mass profile data can be correlated with reference mass profiles to detect (or determine) the presence or absence of at least one biomarker associated with HPV infection. This procedure is also referred to as protein finger printing. The quantity of the biomarker(s) can be also determined as an option.

With respect to the method for diagnosing HPV infection in a subject, for purposes of the present invention, the subject is an animal or a biological sample obtained from the animal. Since HPV infection is most relevant to human beings, the present invention finds its most pertinent utility with detecting or diagnosing HPV in humans (i.e., male or female human subjects). The biological sample can be blood, serum, urine, prostatic fluid, seminal fluid, semen, tissue extract sample, or biopsy. It should be understood that a tissue extract sample can include, for example, samples obtained from the cervix of a subject using a swab, brush, or other suitable materials for collecting a sample.

In the present invention, HPV infection is detected by determining the presence or absence of one or more biomarkers associated with HPV infection. The present invention is most useful in that it can detect the presence or absence of more than one biomarker from the same sample in the same analysis. Thus, unlike previous conventional HPV infection detection methods, the present invention provides the ability to conduct a single test which can determine the presence or absence of more than one biomarker, such as at least two biomarkers, at least three biomarkers, at least four biomarkers, at least five biomarkers, or all biomarkers associated with HPV infection in a single test or analysis without the need to run two or more separate assays in order to determine the presence or absence of each individual biomarker. Thus, the present invention provides a method that permits a comprehensive single test that permits a full determination of the presence or absence of two or more or all biomarkers associated with HPV infection and/or further permits the identification of the presence or absence of each biomarker at the same time. Thus, not only can more than one and, preferably, all biomarkers be analyzed for their presence or absence, but the present invention permits one to know which particular biomarkers are present and which particular biomarkers are absent, that are associated with HPV infection. By knowing the particular biomarkers that are present or absent, not only can a determination be made that a person has HPV infection, but a determination can be made on the type of HPV infection that a subject has, whether the HPV infection is in an early stage or late stage, and/or whether the HPV infection is of a greater severity or not based on the particular biomarkers present.

As described above, HPV infection is a group of DNA viruses and are the etiologic agents of epithelial out-growths or papillomas. Various proteins or fragments thereof are known to be associated with HPV. In the present invention, using mass spectrometry or other techniques that gather mass profile data, one is capable of determining the presence or absence of these biomarkers associated with HPV. Each of the biomarkers associated with HPV will have a different mass-to-charge ratio or individual mass spectrum. Each of these biomarkers can be analyzed for their specific mass-to-charge ratio. It is noted that even modified forms of the peptides, polypeptides, or proteins can be identified and distinguished based on their respective mass-to-charge ratio numbers or similar data achieved through a mass analyzer, such as a mass spectrometer. Thus, with the present invention, a sample can be analyzed.

A biomarker associated with HPV can be any peptide, protein, or polypeptide generally known in the art to indicate HPV infection when present or when present at elevated levels in a biological sample from a subject. A biomarker can be associated with oncogenic forms of HPV. A biomarker associated with oncogenic forms of HPV can be a peptide, protein, or polypeptide encoded in the early coding regions of oncogenic forms of HPV. A biomarker associated with oncogenic forms of HPV can be a peptide, protein, or polypeptide encoded by the E2, E5, E6, E7, or E8 coding regions of oncogenic HPV strains. It should be understood that proteins encoded by the E2, E5, E6, E7, or E8 coding regions of HPV can be referred to as "E2 proteins," "E5 proteins," "E6 proteins," "E7 proteins," or "E8 proteins" respectively. Each of these biomarkers have a different mass-to-charge ratio or different individual mass spectrum that is distinguishable from each other.

The HPV infection associated with the biomarker can be oncogenic HPV or an oncogenic form of HPV. The oncogenic forms of HPV can include, for example, HPV type 16, 18, 45, 33, 31, 58, 52, 35, 51, 59, 56, 68, 73, 39, 66, 82, 26, 30, 53, or 69. Oncogenic HPV, oncogenic forms of HPV, or oncogenic HPV strains, as used herein, refers to high risk variants of HPV which cause or tend to cause cervical cancer, penile cancer, anal cancer, and throat cancer, for example. A subject "infected" with oncogenic HPV is a subject having cells that contain oncogenic HPV. The oncogenic HPV in the cells may not exhibit any other phenotype (i.e., cells infected with oncogenic HPV do not have to be cancerous). In other words, cells infected with oncogenic HPV may be pre-cancerous (i.e., not exhibiting any abnormal phenotype, other than those that may be associated with viral infection), or cancerous cells.

In the present invention, mass profile data (e.g., mass spectrum or mass-to-charge ratio data) is generated or obtained from a biological sample. As stated, the biological sample generally is obtained from an animal, such as a human being, and the biological sample is of a sufficient quantity and quality which permits one to obtain mass-to-charge ratio information of the molecules present in the sample. The biological sample can be further processed, such as by enzymatically digesting the proteins present into smaller peptides using an agent such as trypsin or pepsin or other proteolytic agents. Essentially, a top-down strategy of protein analysis or a bottom-up approach to protein analysis can be obtained from the biological sample. The biological sample can be further processed by various purification or other preparation techniques as described herein or are conventional in biological sample preparation. The biological sample can be prepared in any conventional manner useful for protein characterization and/or providing mass spectra data or mass-to-charge ratio data.

Mass profile data can comprise one or more discrete, non-background noise peaks that are defined by their mass-to-charge ratio and are characteristic of an individual mass spectrum. The phrases "mass to charge ratio," "m/z ratio," or "m/z" can be used interchangeably and refer to the ratio of the molecular weight (grams per mole) of an ion detected to the number of charges the ion carries. The mass-to-charge ratio can be determined by a gas phase ion spectrometer. A gas phase ion spectrometer refers to an apparatus that measures a parameter which can be translated into mass-to-charge ratios of ions formed when a sample is ionized into the gas phase. Generally, ions of interest bear a single charge, and mass-to-charge ratios are often simply referred to as mass. The gas phase ion spectrometer can be a mass spectrometer, an ion mobility spectrometer, or a total ion current measuring device.

The mass profile data can take the form of mass spectrum, for instance, as shown in FIG. 1, which correlates m/z to intensities. The mass profile data can take any form as long as the mass profile data is sufficient to correlate reference mass profiles in order to determine the presence or absence of one or more biomarkers in the biological sample. The mass profile data can be based on or take the form of selected ion monitoring (SIM), total ion current (TIC), base peak intensity (BPI), and/or selected reaction monitoring (SRM).

With respect to correlating the mass profile data to reference mass profiles, the term "reference mass profiles" includes mass profiles of biological samples or reference biological samples, obtained from subjects having a known HPV classification. In other words, the reference biological samples can be obtained from subjects known not to have HPV infection, known to have HPV infection, or known to have a specific stage or strain of HPV infection. The reference mass profile is essentially one method or means to determine whether one or more biomarkers associated with HPV infection are present. By having a library of reference mass profiles, wherein each reference mass profile is a profile of a particular protein or peptide or polypeptide, or a fragment thereof or other biomarker associated with HPV infection, these reference mass profiles can then be compared to the mass profile data from the biological sample to determine if any matches occur, thereby providing the ability to determine the presence or absence of each biomarker. Thus, in one embodiment of the present invention, the reference mass profiles can include profiles for one, a few, or each known strain or protein or peptide associated with HPV and, thereby a comparison can be made with this known library to determine the presence or absence of any of these peptides, proteins, or polypeptides associated with HPV in the biological sample. The determination of whether HPV infection is present in a biological sample by an understanding of the mass profile data from the biological sample can be achieved by any means, such as visual review of the mass profile data, a comparison conducted by a computer program (or electronically) with known mass profiles or reference mass profiles. This comparison or determination can be automated, as with a computer program/software. This comparison of the mass profile data from the biological sample with reference mass profiles can occur in the form of mass spectra or simply a search of various mass-to-charge ratio numbers and the like.

As stated, this comparison of the mass profile data of the biological sample with known profile data of HPV infection not only can permit one to determine the presence or absence of HPV infection in general in a sample and the subject involved, but permits one to know exactly which peptide, polypeptide, or protein is present, thereby permitting one to know the exact HPV protein present and, therefore, a determination of whether the HPV infection is at an early stage or late stage can be made, as well as other determinations based on this information. In addition, with the present invention, not only can the native form of the peptides, polypeptides, or proteins can be determined, but the peptides, polypeptides, or proteins in their denatured or post-translational modified forms can be detected, as well as partially fragmented proteins, as well as intact proteins. By having the ability to detect all of these various types and forms of proteins, peptides, and polypeptides, a comprehensive understanding of the biological sample can occur in a single test, whereas an immunoassay would require multiple runs or a protein array without cross-reactions.

Thus, various forms of peptides, proteins, and polypeptides associated with HPV can be detected resulting from either or both of pre- and post-translational modification. Pre-translational modified forms include allelic variants, splice variants and/or RNA editing forms. Post-translationally modified forms include forms resulting from proteolytic cleavage (e.g., cleavage of a signal sequence or fragments of a parent protein), glycosylation, phosphorylation, lipidation, oxidation, methylation, cysteinylation, sulphonation, and/or acetylation.

Further, with the present invention, not only can different peptides, proteins, or polypeptides be detected based on mass-to-charge ratios, for instance, ranging from a few hundred to over a half-million, the present invention has the ability to detect various forms of the same peptide, protein, or polypeptide and, further, has the ability to distinguish between these forms, which is also useful in understanding the nature of the HPV infection, if present, in the biological sample.

The presence or absence of at least one biomarker in a biological sample from a subject can indicate whether the subject is infected or not infected with HPV. According to one or more embodiments, the quantity and/or the presence or absence of a biomarker can further indicate the strain and/or the stage of HPV infection. As an example, a particular biomarker or group of different biomarkers is present only in biological samples from patients infected with oncogenic HPV. Mass profiling of two biological samples from different subjects, X and Y, reveals the presence of the biomarker or group of different biomarkers in a sample from test subject X, and the absence of the biomarker or group of different biomarkers in a test sample from subject Y. The medical practitioner can diagnose subject X as being infected with oncogenic HPV and subject Y as not being infected with oncogenic HPV. If the biomarker or group of different biomarkers are present only in biological samples from patients infected with a specific strain of oncogenic HPV, a medical practitioner can also identify the specific strain of oncogenic HPV infection in subject X. If the biomarker or group of different biomarkers are only present in patients when oncogenic HPV infection has progressed to a particular stage, a medical practitioner can also identify the specific stage of oncogenic HPV infection in a subject.

Any suitable mass analyzer, such as a mass spectrometer, can be used. A time-of-flight mass analyzer, a sector field mass analyzer, a quadrupole mass analyzer, Orbitrap analyzer, Fourier transform ion cyclotron resonance analyzer, and/or tandem mass spectrometry can be used. The biomarkers can be ionized by an ionization source such as a laser, the generated ions are collected by an ion optic assembly, and then a mass analyzer disperses and analyzes the passing ions. The detector then translates information of the detected ions into mass-to-charge ratios.

The biomarkers can be detected in a gas phase ion spectrometer. According to various embodiments, the gas phase ion spectrometer can comprise a mass spectrometer. Mass spectrometry allows for detection of biomarkers associated with HPV in a biological sample, and overcomes many problems associated with conventional methods for diagnosing or detecting HPV infection. With mass spectrometry, analytes in a biological sample can be directly subjected to ionization of choice in a mass spectrometer. The resulting spectrum can show m/z ratio or time of flight for all the proteins.

The mass-to-charge ratios can be determined, for example, from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers can be determined using, for example, Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two.

The mass spectrometry, which can be used to detect the presence or absence of a biomarker, can be matrix-assisted laser desorption ionization/time of flight (MALDI-TOF), surface enhanced laser desorption ionization time of flight (SELDI-TOF), liquid chromatography, tandem mass spectrometry (MS-MS), electrospray ionization (ESI-MS), or desorption electrospray ionization (DESI). One type of DESI that can be used in the present invention is chemical ionization or desorption atmospheric pressure chemical ionization (DAPCI). The mass spectrometer can be a laser desorption/ionization mass spectrometer (LDI).

"Surface Enhanced Laser Desorption and Ionization" or "SELDI," as described, for example, in U.S. Pat. Nos. 5,719,060 and 6,225,047, can be used to detect at least one biomarker. This refers to a method of desorption/ionization gas phase ion spectrometry (e.g., mass spectrometry) in which an analyte (here, one or more of the biomarkers) is captured on the surface of a SELDI mass spectrometry probe. SELDI is also referred to as "affinity capture mass spectrometry" or "Surface-Enhanced Affinity Capture" ("SEAC"). This version involves the use of probes that have an adsorbent on the probe surface that captures biomarkers through a non-covalent affinity interaction (adsorption) between the material and the biomarker. Such probes can be referred to as "affinity capture probes" and as having an "adsorbent surface."

Another method of laser desorption mass spectrometry is called Surface-Enhanced Neat Desorption ("SEND"). The EAM category includes molecules used in MALDI, frequently referred to as "matrix," and is exemplified by cinnamic acid derivatives, sinapinic acid (SPA), cyano-hydroxycinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition can be a co-polymer of α-cyano-4-methacryloyloxycinnamic acid, acrylate and 3-(tri-ethoxy)silyl propyl methacrylate. In another embodiment, the composition can be a co-polymer of α-cyano-4-methacryloyloxycinnamic acid and octadecylmethacrylate ("C18 SEND"). SEAC/SEND can be used and is a version of laser desorption mass spectrometry in which both an adsorbent and an energy absorbing molecule are attached to the sample presenting surface. Another version of LDI that can be used is Surface-Enhanced Photolabile Attachment and Release ("SEPAR").

Generating mass profile data for the biological sample can comprise contacting the biological sample with at least one adsorbent and detecting at least one biomarker bound to the at least one adsorbent using gas phase ion spectrometry. An "adsorbent" can be considered a "capture reagent," an "affinity reagent" or a "binding moiety." The adsorbent can be any material capable of binding a biomarker. In certain embodiments, probes have the adsorbent already attached to the surface. In other embodiments, the probes are pre-activated and include a reactive moiety that is capable of binding the adsorbent, e.g., through a reaction forming a covalent or coordinate covalent bond. Epoxide and acyl-imidizole are useful reactive moieties to covalently bind polypeptide adsorbents, such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

An adsorbent can comprise a chromatographic adsorbent. A chromatographic adsorbent refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

An adsorbent can comprise a biospecific adsorbent. A biospecific adsorbent refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane, or a virus. Examples of biospecific adsorbents are antibodies, receptor proteins, and nucleic acids. Biospecific adsorbents typically have higher specificity for a target analyte than chromatographic adsorbents.

Biospecific adsorbents can comprise PDZ domain proteins. Biospecific adsorbents can comprise PDZ domain polypeptides. PDZ domain proteins and polypeptides, unlike antibodies, can bind most or all forms of oncogenic HPV E6 proteins. Oncogenic forms of E6 protein can recognize the PDZ domain of *Drosophila* tumour suppressor protein, discs large (Dlg), for example, and binding of HPV E6 proteins to Dlg correlates with the oncogenic potential of these viruses (Gardiol et al., *Oncogene* 18: 5487-5496 (1999)). Examples of PDZ domain proteins and polypeptides, which can bind to oncogenic HPV E6 proteins, are provided in International Publication No. WO 2004/022006 (Lu et al.), which is incorporated by reference herein in its entirety.

Data analysis can include the steps of determining signal strength (e.g., intensity of peaks) of a biomarker(s) detected and optionally removing "outliers" (data deviating from a predetermined statistical distribution). In an embodiment, an observed signal for a given peak can be expressed as a ratio of the intensity of that peak over the sum of the entire observed signal for both peaks and background noise in a specified mass to charge ratio range. In an embodiment, a standard may be admitted with a sample so that a peak from the standard can be used as a reference to calculate relative intensities of the signals observed for each biomarker(s) detected.

A probe or mass spectrometry probe can comprise a device that is removably insertable into a gas phase spectrometer and comprises a substrate having a surface for presenting analytes for detection. A probe can comprise a single substrate or a plurality of substrates. Terms such as ProteinChip™, ProteinChip™ array, sample presenting surface, chip, or biochip are also used herein to refer to probes or specific kinds of probes.

The biological sample can be purified prior to the step of generating mass profile data for the biological sample. Biomarkers can be first captured with biospecific (e.g., an antibody) or chromatographic materials coupled to a solid support such as a resin (e.g., in a spin column). According to at least one embodiment, the biological sample is subjected to a hydrophobic column. After purification, the biomarkers are eluted and then detected by MALDI or mass analyzers.

A probe with an adsorbent surface can be contacted with a biological sample to allow the biomarker or biomarkers that may be present in the biological sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and/or temperature. Unless the probe has both SEAC and SEND properties (as described herein), an energy absorbing molecule then is applied to the substrate with the bound biomarkers.

The mass spectrometry can be combined with immunoassay. First, a biospecific adsorbent (e.g., an antibody, aptamer or Affibody that recognizes the biomarker and other forms of it) is used to capture the biomarker of interest. Preferably, the biospecific adsorbent is bound to a solid phase, such as a bead, a plate, a membrane or an array. After unbound materials are washed away, the captured analytes are detected and/or measured by mass spectrometry. Various forms of mass spectrometry are useful for detecting the protein forms, including laser desorption approaches, such as traditional MALDI or SELDI, and electrospray ionization.

A sample can be analyzed by means of a biochip. Biochips generally comprise solid substrates and have a generally planar surface, to which an adsorbent is attached. Frequently, the surface of a biochip comprises a plurality of addressable locations, each of which has the adsorbent bound there. Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK).

Any suitable protein biochip known in the art can be used, including, for example, protein biochips produced by Ciphergen. Protein biochips can comprise surfaces having chromatographic or biospecific adsorbents attached thereto at addressable locations. Ciphergen's ProteinChip™ arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine funtionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

The biomarkers can be captured with a solid-phase bound immuno-adsorbent that has antibodies that bind the biomarkers. After washing the adsorbent to remove unbound material, the biomarkers are eluted from the solid phase and detected by applying to a SELDI biochip that binds the biomarkers for analyzing by SELDI.

As indicated, the mass profile data for the biological sample can be correlated with a reference mass profile by transforming the mass profile data into a computer readable form and comparing the computer readable form of the mass profile data with a database containing the reference mass profile. A database comprising mass profiles specific for healthy subjects and subjects infected with HPV can be generated by contacting biological samples isolated from said subjects with an adsorbent on a sample presenting surface under specific binding conditions, allowing the biomarkers within said sample to bind said adsorbent, detecting one or more bound biomarkers using a detection method wherein the detection method generates a mass profile of said sample, transforming the mass profile data into a computer-readable form and applying a mathematical algorithm to classify the mass profile as specific for subjects not infected with HPV and subjects infected with HPV. A mass profile specificity can be differentiated into patients known not to be infected with HPV, patients known to be infected with HPV and the particular strain of HPV infection, and patients known to be infected with HPV and the particular stage of HPV infection. An increase in the data characterized (i.e., number of patients entered into the database) would result in an improvement in the diagnostic accuracy of the database.

Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

A method for detecting at least one biomarker associated with HPV infection in a biological sample can comprise contacting a biological sample with at least one adsorbent and detecting the presence or absence of at least one biomarker bound to the at least one adsorbent using gas phase ion spectrometry, wherein the at least one biomarker is a peptide, protein, or polypeptide encoded by the E2, E5, E6, E7, or E8 regions of HPV. According to some embodiments, the method for detecting at least one biomarker in a biological sample can comprise detecting two or more biomarkers bound to the at least one adsorbent using gas phase ion spectrometry.

A method for diagnosing human pappillomavirus (HPV) infection in a subject can comprise obtaining a biological sample from the subject, determining the mass profile of the biological sample using mass spectrometry, transforming the mass profile into a computer readable form, and comparing the mass profile in computer readable form with a database comprising a reference mass profile to detect the presence of at least one biomarker associated with HPV infection, whereby the presence of the at least one biomarker associated with HPV infection can indicate the presence or absence of HPV infection in the subject.

One or more biomarkers associated with HPV infection can be detected by a method commonly known as peptide mass fingerprinting (PMF). In PMF, individual molecular weight values of peptide fragments generated by enzymatically digesting known proteins are measured and are recorded in a database in advance as molecular weights of peptide fragments for reference. The proteins are digested by a proteolytic enzyme such as trypsin. An isolated target protein in a biological sample to be analyzed by mass spectrometry, is subjected to peptide fragmentation by the same enzymatic digestion. Respective molecular weights of the peptide fragments of the target protein in the biological sample are then compared with the individual molecular weights of the peptide fragments recorded in the database in order to identify the target protein. A match of a peptide fingerprinting pattern of a biological sample with a peptide fingerprinting pattern of one or more types of HPV peptides in the pre-established database can be used to diagnose HPV and HPV subtypes.

A target protein to be analyzed can be enzymatically digested in advance, with a proteolytic enzyme having specificity to cleavage sites. Individual molecular weights of generated peptide fragments are determined by mass spectrometry. Then, based on this information of the first mass spectrometry, predicted molecular weights of peptide fragments presumptively generated by similar peptide fragmentation performed on the known proteins are calculated from sequence information about their (deduced) full-length amino acid sequences recorded in the database and compared with the individual molecular weights of the actually measured peptide fragments to identify the target protein.

A method for detecting at least one biomarker in a biological sample can comprise isolating at least one target peptide, protein, or polypeptide from a biological sample, digesting the at least one target peptide, protein, or polypeptide into at least two fragments using a proteolytic enzyme, generating mass profile data for the at least two fragments using gas phase ion spectrometry, and comparing the mass profile data for the at least two fragments with mass profile data of peptide fragments resulting from proteolytic digestion of at least one biomarker associated with HPV infection. Examples of proteolytic enzymes include trypsin, chymotrypsin, papain, and bromelain. According to at least one embodiment, the peptide, protein, or polypeptide can by digested by trypsin.

One or more biomarkers can be detected within a given biological sample. One or more biomarkers in a biological sample can bind to an adsorbent under specific binding conditions following little or no sample preparation or treatment. More than one biomarker in a biological sample can bind to an adsorbent under specific binding conditions. For example, a given sample can be applied directly to a sample presenting surface comprising an adsorbent consisting of cationic quaternary ammonium groups and the biomarkers within the given sample that are detected using mass spectrometry. In some embodiments, biomarkers can be isolated and further characterized using standard laboratory techniques before the biomarkers are applied to a sample presenting surface.

A mass profile of a sample can be generated using a liquid-chromatography (LC)-based assay in which biomarker(s) of a given sample are bound by biochemical or affinity interactions to an adsorbent located in a vessel made of glass, steel, or synthetic material; known to those skilled in the art as a chromatographic column. The biomarker(s) are eluted by washing the vessel with appropriate solutions known to those skilled in the art. Such solutions include but are not limited to, buffers, e.g. Tris(hydroxymethyl)aminomethane hydrochloride (TRIS-HCl), buffers containing salt, e.g. sodium chloride (NaCl), or organic solvents, e.g. acetonitrile. Mass profiles of these biomarkers are generated by application of the eluting biomarkers of the sample by direct connection via an electrospray device to a mass spectrometer (LC/ESI-MS).

Conditions that promote binding of a biomarker(s) to an adsorbent are known to those skilled in the art and ordinarily include parameters such as pH, the concentration of salt, organic solvent, or other competitors for binding of the biomarker to the adsorbent.

A mass spectrometer can be used to detect a biomarker(s) on a chip. In a typical mass spectrometer, a chip with a bound biomarker(s) co-crystallized with an energy absorbing molecule is introduced into an inlet system of a mass spectrometer. The energy absorbing molecule:biomarker crystals are then ionised by an ionization source, such as a laser. The ions generated are then collected by an ion optic assembly, and then a mass analyser disperses and analyses the passing ions. The ions exiting the mass analyser are then detected by an ion detector. The ion detector then translates the information into mass-to-charge ratios. Detection of the presence of a biomarker(s) or other substances will typically involve detection of signal intensity. This, in turn, can reflect the quantity and character of a biomarker bound to the probe.

Thus, mass spectrometry can be used to detect biomarkers associated with HPV in a given biological sample. Such methods include, but are not limited to, matrix-assisted laser desorption ionization/time-of-flight (MALDI-TOF), surface-enhanced laser desorption ionization/time-of-flight (SELDI-TOF), liquid chromatography coupled with MS, MS-MS, or ESI-MS. Typically, biomarkers are analysed by introducing a sample presenting surface containing said biomarkers, ionising said biomarkers to generate ions that are collected and analysed.

The present invention is further illustrated by the following example, which should not be construed as limiting in any way. The contents of all cited references (including literature references, issued patents, published patent applications), as cited throughout this application, are hereby expressly incorporated by reference. The practice of the present invention will employ, unless otherwise indicated, conventional techniques of cell biology, cell culture, molecular biology, transgenic biology, microbiology, recombinant DNA, and immunology, which are known to those skilled in the art. Such techniques are explained fully in the literature.

EXAMPLE

Clinical Sample Processing and Protein Extractions

The following six samples were processed and introduced into a mass spectrometer for detecting the presence of E6 protein from HPV16:

| | |
|---|---|
| Sample 1: | 0.1 N NaOH unneutralized C33A+ supe |
| Sample 2: | 1 M Urea in Tris Glycine pH 11.5 C33A+ Supe |
| Sample 3: | 0.1 M Urea in Tris Glycine w/0.05% SDS pH 11.5 C33A+ Supe |
| Sample 4: | 0.1 N NaOH unneutralized C33A− supe |
| Sample 5: | 1 M Urea in Tris Glycine pH 11.5 C33A− Supe |

-continued

| | |
|---|---|
| Sample 6: | 0.1 M Urea in Tris Glycine w/0.05% SDS pH 11.5 C33A− Supe |

Samples 1-3 include differently treated cells from a cervical cancer cell line that were infected with E6 protein (C33A+). E6 proteins can have a mass range of about 16,000 m/z to about 19,000 m/z. Samples 4-6 include differently treated cells from a cervical cancer cell line that does not produce the E6 protein (C33A−).

Cells from each sample were added to a microcentrifuge tube (commercially available from Eppendorf AG). The tubes were centrifuged at 1500 rpm, for approximately 15 minutes. The supernatant was removed and discarded. A reducing reagent (DTT/PI) was added. The pellet was extracted with equal volume ER and rocked for 30 minutes at room temperature. The tubes were centrifuged at 20,000×g (gravity) for approximately 15 minutes. The supernatant was again removed and discarded. The pellet was resuspended in equal volume of ER.

The clinical samples were subjected to a hydrophobic column such as C4 or C18 Ziptip™ (commercially available from Millipore™) by a standard operation protocol known to those skilled in the art to remove a majority of salts, buffers, solubilization enhancers or denaturing agents such as urea, guanidine or detergents, prior to introduction into a mass spectrometer. The previously cleaned samples were then introduced into a mass spectrometer.

The mass spectral data for samples 1 and 4, described in the Example, are depicted in FIG. 1. Two sets of data are shown for sample 1 and sample 4 because the two samples were introduced into a mass spectrometer on two different occasions, and each time a different mass spectrometer was used. Peaks 16390.3 m/z and 16419.4 m/z, shown in FIG. 1, indicate the presence of E6 in sample 1. The differing m/z values for sample 1 can be attributed to use of different mass spectrometers. The mass spectral data for sample 4 does not indicate the presence of any peaks that are within the 16,000 mz to 19,000 m/z mass range. The absence of these peaks for sample 4 indicates the absence of E6 in sample 4.

Figure 2:
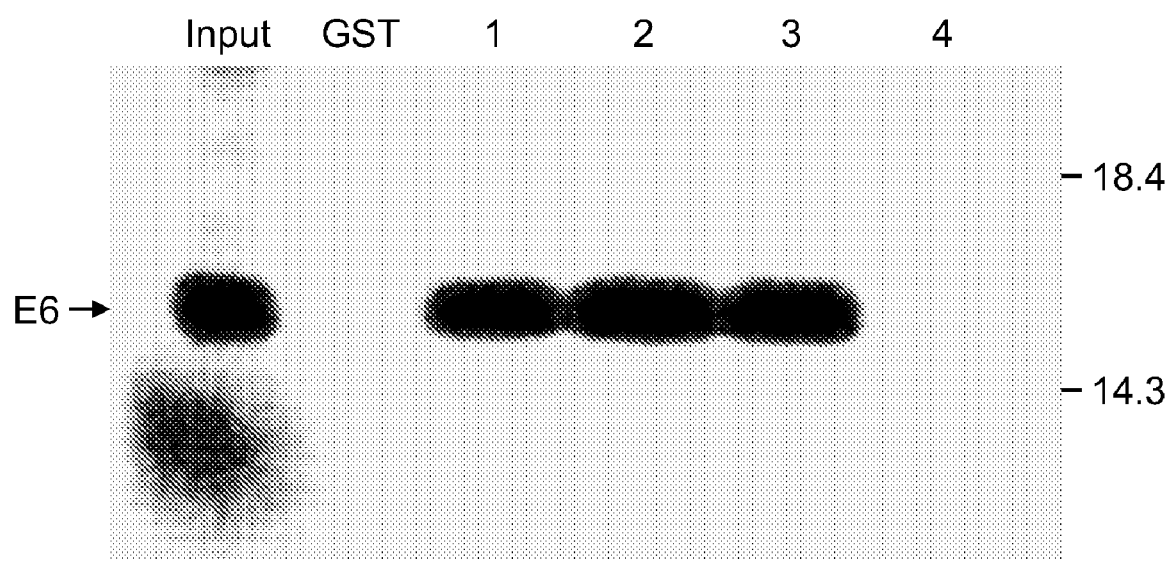
FIG. 2 shows electrophoresis results for four different clinical samples containing cells from a cervical cancer cell line.

FIG. 2 depicts electrophoresis results of samples 1-4. The input lane or positive control lane indicates the molecular weight of E6 protein from HPV 16. Lanes 1-4 indicate the presence of E6 protein in samples 1-3 and the absence of E6 protein in sample 4.

It should be understood that with the help of robotic sample preparation and autosampler or autoloader, multiple samples can be screened on a single chip or platform.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed:

1. A method for diagnosing human papillomavirus (HPV) infection in a subject comprising:
   a) generating a peptide fingerprinting pattern by peptide mass fingerprinting (PMF) for at least one target protein in a biological sample from the subject; and
   b) determining the presence or absence of at least one biomarker associated with HPV infection in the biological sample by correlating the peptide fingerprinting pattern of the target protein with a known peptide fingerprinting pattern of at least one biomarker associated with HPV infection;
   wherein the at least one biomarker is a protein encoded by the E2, E5, E6, E7, or E8 regions of oncogenic forms of HPV;
   whereby a match of the peptide fingerprinting pattern of the target protein with the known peptide fingerprinting pattern indicates the presence of at least one biomarker in the sample;
   whereby the presence of the at least one biomarker associated with HPV infection in the biological sample indicates HPV infection in the subject.

2. The method of claim 1, wherein the presence or absence of at least two biomarkers associated with HPV infection is determined from the peptide fingerprinting pattern.

3. The method of claim 1, wherein the quantity or presence of the at least one biomarker associated with HPV infection indicates the stage of HPV infection in the subject.

4. The method of claim 1, wherein the HPV is HPV type 16 18, 31, 33, 35, 45, 51, 52, 56, 59, 68, 73, 39, 66, 82, 26, 30, 53, 69, or 58.

5. The method of claim 1, wherein the biological sample is blood, serum, urine, prostatic fluid, seminal fluid, semen, tissue extract sample, or biopsy.

6. The method of claim 1, wherein the subject is a woman.

7. A method for detecting at least one biomarker associated with HPV infection in a biological sample comprising:
   a. digesting at least one biomarker into at least two peptide fragments using a first proteolytic enzyme, said biomarker being E2, E5, E6, E7, and/or E8 protein;
   b. generating a mass spectrum for the at least two biomarker peptide fragments using mass spectrometry to obtain a reference mass spectrum;
   c. recording the mass spectrum for the at least two biomarker peptide fragments
   d. isolating at least one target protein in the biological sample;
   e. digesting the at least one target protein in the biological sample into at least two peptide fragments using a second proteolytic enzyme, the second proteolytic enzyme being the same kind of proteolytic enzyme as the first proteolytic enzyme;
   f. generating a mass spectrum for the at least two peptide fragments of the biological sample using mass spectrometry;
   g. correlating the mass spectrum for the at least two peptide fragments of the biological sample with the reference mass spectrum of the biomarker;
   whereby a match of the mass spectrum for the at least two peptide fragments of the biological sample and the reference mass spectrum indicates the presence of the biomarker in the biological sample.

8. The method of claim 7, wherein the mass spectrometry is matrix-assisted laser desorption ionization/time of flight (MALDI-TOF), surface enhanced laser desorption ionization time of flight (SELDI-TOF), liquid chromatography coupled with mass spectrometry, tandem mass spectrometry (MS-MS), electrospray ionization (ESI-MS), or chemical ionization.

9. The method of claim 7, wherein the step of correlating the mass spectrum for the at least two peptide fragments of the sample with the reference mass spectrum comprises:
   a) transforming the mass spectrum obtained in step (f) into a computer readable form; and
   b) comparing the computer readable form of the mass spectrum obtained in step (f) with a database containing the reference mass spectrum.

10. The method of claim 7, wherein the step of correlating the mass profile data for the sample with a reference mass profile further indicates the strain of HPV infection in the subject.

* * * * *